April 2, 1946. E. S. BOERNER Plant Pat. 672
ROSE PLANT
Filed May 17, 1945
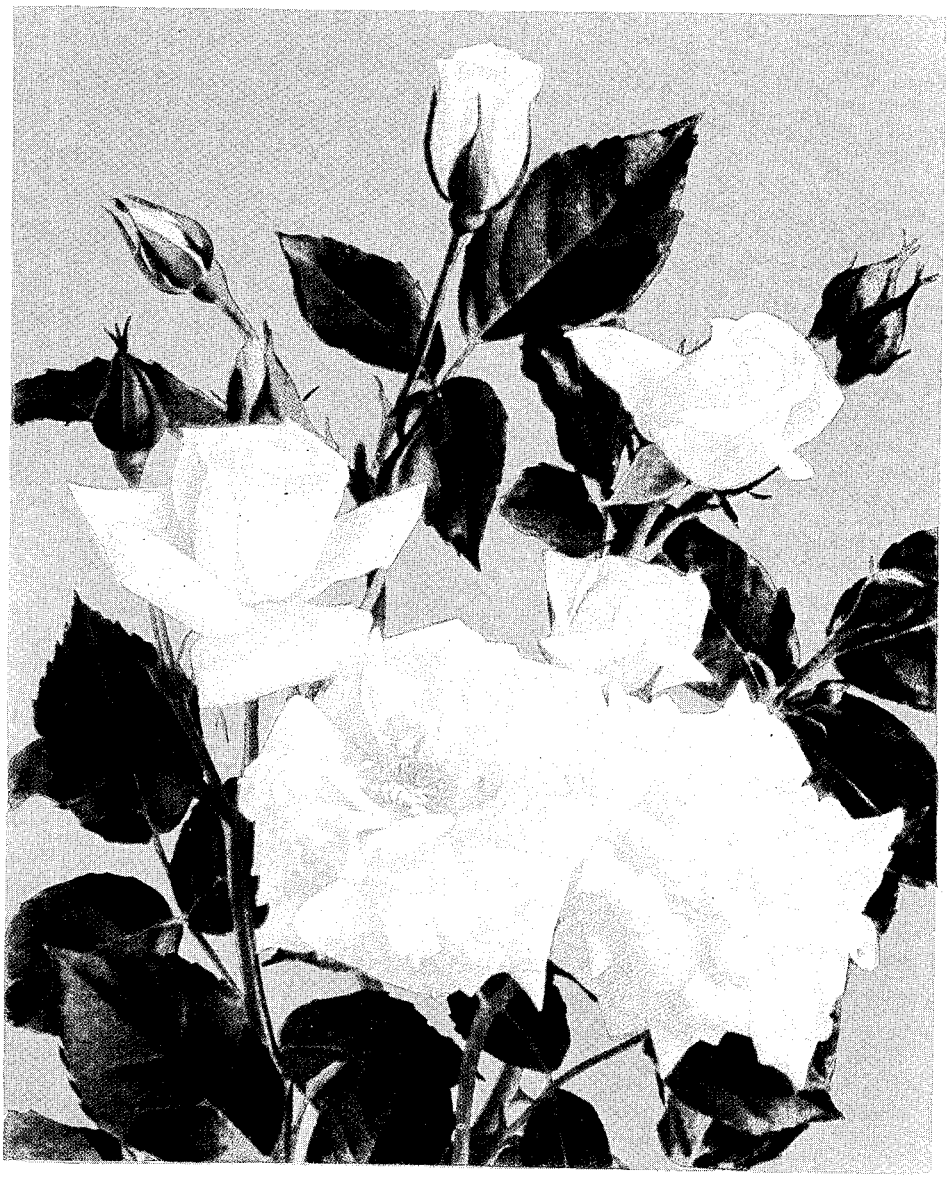
Inventor
E. S. Boerner
By Robbins & Robb
His Attorneys Patented Apr. 2, 1946

Plant Pat. 672

UNITED STATES PATENT OFFICE

672

ROSE PLANT

Eugene S. Boerner, Newark, N. Y., assignor to Jackson & Perkins Company, Newark, N. Y., a corporation of New York Application May 17, 1945, Serial No. 594,294

1 Claim. (Cl. 47—61)

The present invention relates to a new and distinct variety of rose plant, of the Floribunda class, originated by crossing of a semi-climbing seedling and the well known climbing rose "Doubloons" (Plant Patent 152). The latter variety is characterized by its vigorous and hardy habit of growth, its production of large golden flowers, and spicy, clean fragrance.

It was the object of the present invention to incorporate as many of these desirable and valuable characteristics as possible in a rose of the Polyantha class and as a result of the cross aforesaid, this new variety displays a number of important improvements, among the primary of which is its exquisite composition of golden yellow of the bloom and attractive shiny dark green foliage, illustrated as nearly as possible to depict in the accompanying drawing.

For a Floribunda rose, it is notable for the permanence of its coloring, that is, the ability of the blooms to retain their color throughout all of the stages of their development, unlike previous similar varieties that show the yellow shade in the bud and partially opened flower only.

Another important feature of this new Floribunda is its rugged characteristic of producing flowers under extreme conditions of heat and drought.

In growth habit, this plant is of bush form with dense spreading foliage, quite resistant to blackspot.

The buds of this new rose are rounded in form, developing into fully petalled flowers, growing in rather flat clusters, and these flowers possess a moderate fruity fragrance.

The foregoing dominant characteristics of this new variety, among others referred to in the following detailed description, have been found to be established by asexual reproduction. (Color terminology accords with Ridgway's Color Standard.)

Parentage: Seedling.
- *Seed parent.*—Semi-climbing seedling.
- *Pollen parent.*—"Doubloons."

Classification:
- *Botanic.*—Large-flowered Polyantha.
- *Commercial.*—Floribunda.

*Flower*

(Observations made in the fields of Jackson & Perkins Company, Newark, New York, in the afternoon in the month of September, 1944.)

Blooming habit: Recurrent—continuous.

Bud:
- *Size.*—Medium.
- *Form.*—Ovoid. Is not affected by wet or hot weather.
- *Color.*—When sepals first divide—Light Greenish Yellow, Plate V; when petals begin to unfurl—Empire Yellow, Plate IV; when half blown—inside of petals, Pale Lemon Yellow, Plate IV; reverse of petals, Martius Yellow, Plate IV.
- *Sepals.*—Branched, "hood" above bud. Curl back when petals begin to unfurl. *Color*—outside—Oil Green, Plate V, tinged with Garnet Brown, Plate I; inside—Light Lumiere Green, Plate XVII.
- *Calyx.*—Shape—pear. Size—small. Aspect—smooth. Color—Parrott Green, Plate VI.
- *Peduncle.*—Length—medium. Aspect—smooth. Color—Mars Brown, Plate XV. Strength—bending; slender.
- *Opening.*—Opens up well. Is not affected by adverse conditions.

Bloom:
- *Size.*—Medium. Average size when fully expanded, 3½".
- *Borne.*—In clusters; flat.
- *Stems.*—Medium length; normal strength.
- *Form.*—Cupped in early stages which opens to a flat flower with the lower petals reflexed. Permanence—retains its form to the end.
- *Petalage.*—Double (full but open center). Number of petals under normal conditions, 45.
- *Color.*—Center of flower—Empire Yellow, Plate IV. Outer petals—Barium Yellow, Plate XVI. Base of petals (aiglet)—Pale Lemon Yellow, Plate IX. Inside of petals—Citron Yellow, Plate XVI, with lower half of petal Pale Lemon Yellow, Plate IV. Reverse of petals—Barium Yellow, Plate XVI. General tonality from a distance—Citron Yellow, Plate XVI.
- *Discoloration.*—General tonality at end of first day—Citron Yellow, Plate XVI. Second day—between Citron Yellow, Plate XVI, and Barium Yellow, Plate XVI. Third day—Barium Yellow, Plate XVI.

Petals:
- *Texture.*—Thick. Is not affected by wet or hot weather.
- *Appearance.*—Inside—satiny. Outside—shiny.
- *Form.*—Oval; pointed.

*Arrangement.*—Irregular. Petaloids in center—few; small.
*Persistence.*—Drop off cleanly.
*Fragrance.*—Moderate. Nature—fruity (Russet apple).
*Lasting quality.*—On the plant and as cut flower, long.

Genital organs:
*Stamens, anthers.*—Size—medium; few. Color—Apricot Yellow, Plate IV. Arrangement—regular around styles.
*Stamens, filaments (threads).*—Length—medium. Color—Pale Lemon Yellow, Plate IV.
*Pollen.*—Maize Yellow, Plate IV.
*Styles.*—Columnar, even; medium length; thin.
*Stigmas.*—Pinard Yellow, Plate IV.
*Ovaries.*—Protruding from calyx.

*Plant*

Form: Bush.
Growth: Vigorous; branching.
Foliage: 5 leaflets.
*Size.*—Medium.
*Quantity.*—Normal.
*Color.*—New foliage: upper side—Cedar Green, Plate VI; serrations Madder Brown, Plate XIII; under side—Biscay Green, Plate XVII, veined Madder Brown, Plate XIII. Old foliage: upper side—Dark Cress Green, Plate XXXI; under side—Light Cress Green, Plate XXXI.
*Shape.*—Oval pointed.
*Texture.*—Upper side—leathery; glossy. Under side—smooth. Ribs and veins—light.
*Edge.*—Serrated (saw toothed).
*Serration.* Single; small.
*Rachis.*—Light Cress Green, Plate XXXI. Under side—smooth.
*Stipules.*—Medium length; bearded.
*Disease resistance.*—Resistant insofar as this is evidenced by absence of any disease throughout development and establishment of this variety.

Wood:
*New wood.*—Color—Light Bice Green, Plate XVII. Bark—smooth.
*Old wood.*—Color—Elm Green, Plate XVII. Bark—smooth.

Thorns (thorns are divided into thorns, prickles, and short needles):
*Thorns.*—Quantity—on main stalks from base and on laterals from stalk—ordinary. Form—Flat base; medium length; straight. Color when young—Oxblood Red, Plate I. Position—irregular.
*Prickles.*—Quantity—on main stalks and on laterals—none.
*Short needles.*—Quantity—on main stalks and on laterals—none.

I claim:

A new and distinct variety of rose plant of the large flowered Polyantha class, characterized as to novelty by the golden yellow color of its flowers retained throughout all stages of development; the rounded form of bud opening into fully petalled flowers borne in flat clusters; the rugged characteristic of producing flowers under extreme conditions of heat and drought; fruity fragrance of the flowers; and its shiny, dark green, dense and spreading foliage, resistant to blackspot, substantially as shown and described.

EUGENE S. BOERNER.